United States Patent
Hua et al.

(10) Patent No.: US 10,853,900 B2
(45) Date of Patent: Dec. 1, 2020

(54) METHOD AND SYSTEM FOR PREDICTING ADHERENCE TO A TREATMENT

(75) Inventors: Jun Hua, Novato, CA (US); Hui Zhu, Marlborough, MA (US); Catherine V. Orate-Pott, American Canyon, CA (US); David Shellenberger, Corte Madera, CA (US); Deonadayalan Narayanaswamy, Richmond, CA (US); Niranjan A. Shetty, San Diego, CA (US)

(73) Assignee: Fair Isaac Corporation, Roseville, MN (US)

( * ) Notice: Subject to any disclaimer, the term of this patent is extended or adjusted under 35 U.S.C. 154(b) by 769 days.

(21) Appl. No.: 12/638,847

(22) Filed: Dec. 15, 2009

(65) Prior Publication Data

US 2010/0205008 A1     Aug. 12, 2010

Related U.S. Application Data

(60) Provisional application No. 61/151,152, filed on Feb. 9, 2009.

(51) Int. Cl.
| | |
|---|---|
| *G06Q 50/00* | (2012.01) |
| *G06Q 50/24* | (2012.01) |
| *G06Q 50/22* | (2018.01) |
| *G06F 19/00* | (2018.01) |
| *G16H 50/50* | (2018.01) |

(52) U.S. Cl.
CPC ......... *G06Q 50/24* (2013.01); *G06F 19/3456* (2013.01); *G06Q 50/22* (2013.01); *G16H 50/50* (2018.01)

(58) Field of Classification Search
CPC .... G06Q 50/22; G06Q 50/24; G06F 19/3456; G06F 19/3462
USPC .......................................................... 705/2–3
See application file for complete search history.

(56) References Cited

U.S. PATENT DOCUMENTS

| | | | |
|---|---|---|---|
| 2006/0294108 A1* | 12/2006 | Adelson et al. | 707/10 |
| 2008/0162182 A1* | 7/2008 | Cazares et al. | 705/2 |
| 2008/0228525 A1* | 9/2008 | Weickert et al. | 705/3 |
| 2009/0171697 A1* | 7/2009 | Glauser et al. | 705/3 |

* cited by examiner

*Primary Examiner* — Linh Giang Le
(74) *Attorney, Agent, or Firm* — Mintz Levin Cohn Ferris Glovsky and Popeo, P.C.; Mike Van Loy, Esq.; F. Jason Far-hadian, Esq.

(57) ABSTRACT

Data characterizing an individual is received. Thereafter, one or more variables are extracted from the data so that, using a predictive model populated with the extracted variables, a likelihood of the individual adhering to a treatment regimen can be determined. The predictive model is trained on historical treatment regimen adherence data empirically derived from a plurality of subjects. Subsequently, data characterizing the determined likelihood of adherence can be promoted. Related apparatus, systems, techniques and articles are also described.

12 Claims, 11 Drawing Sheets

METHOD AND SYSTEM FOR PREDICTING ADHERENCE TO A TREATMENT

CROSS REFERENCE TO RELATED APPLICATION

The present application claims priority under 35 U.S.C. § 119 to U.S. Provisional Application Ser. No. 61/151,152, filed Feb. 9, 2009, entitled "Method and System For Predicting Adherence to a Treatment" the disclosure of which is incorporated herein by reference.

TECHNICAL FIELD

The subject matter described herein relates to techniques for predicting medication adherence.

BACKGROUND INFORMATION

There is a risk associated with patients and others not adhering to treatment plans or treatment regimens suggested or ordered by a medical professional. First of all, there is a health risk to the patient. In addition, the cost of providing medical care can become higher if a patient fails to comply or adhere to the suggested treatment plan or regimen. For example, a person may take arrhythmia medication for a heart condition. The medication may have some unpleasant side effects. So a younger person, may decide to forgo medication to avoid the unpleasant side effects. The risk associated with not taking the medication is much worse than the side effects. For example, the effectiveness of the heart may drop to a point where the treatment plan has to be altered to prevent heart failure. There are countless other examples associated with medications. Other treatment regimens also need to be adhered to. For example, a young athlete recovering from a knee injury, such as a torn anterior cruciate ligament, may be put on a rehabilitation program requiring painful visits to a physical therapist or painful weight training. If the plan is not adhered to, the recovery time will be slowed and the recovery may not be complete. Thus, the patient risks reinjuring the knee, which can be much more costly and more painful for the patient. Furthermore, reinjuring the knee will result in increased cost to insurance carriers. Thus, there is a need for a system and method for predicting adherence to medical treatments and treatment regimens.

SUMMARY

In one aspect, data characterizing an individual is received. Thereafter, one or more variables are extracted from the data so that a likelihood of the individual adhering to a treatment regimen can be determined using a predictive model populated with the extracted variables. The predictive model is trained on historical treatment regimen adherence data empirically derived from a plurality of subjects. Thereafter, data characterizing the determined likelihood of adherence can be promoted.

A treatment score indicative of the likelihood of adherence to the treatment regimen can be generated and such treatment score can be promoted (e.g., displayed in a GUI, persisted, transmitted to a remote server, etc.). The treatment score can be associated with one of a plurality of messages, the messages correlating to disjoint ranges of the treatment score. Thereafter, transmission of the associated message can be initiated to the individual. A delivery channel can be determined for the associated message and transmission of the message can be sent on such delivery channel.

The treatment score can be associated with one of a plurality of sets of messages. The messages can correlate to disjoint ranges of the treatment score with each set of messages providing sequential guidance to the individual to increase a likelihood of the individual adhering to the medical treatment. Each set of messages can further have an associating timeline for delivery so messages in the set can be individually transmitted messages based on the timeline for delivery.

Additional data characterizing the individual can be received such that at least a portion of the additional data is generated subsequent to initiation by the individual of the treatment regimen. Thereafter, one or more variables can be extracted from the additional data with at least one of the variables being affected by initiation of the treatment regimen. A predictive model populated with the extracted variables from the additional data can be used to determine a likelihood of the individual continuing to adhere to the treatment regimen. Such determined likelihood of the continued adherence can be promoted.

A likelihood of patient response to the treatment regimen can be determined. Such a likelihood can be determined by extracting one or more patient response variables from the data, determining, using a second predictive model populated with the extracted patient response variables, a likelihood of the individual responding to the treatment regimen, the predictive model being trained on historical treatment regimen response data empirically derived from a plurality of subjects, and promoting data characterizing the determined likelihood of the individual responding to the treatment regimen. A patient response score indicative of the likelihood of the individual responding to the treatment regimen can be determined and promoted. The treatment score and the patient response score can be associated with one of a plurality of sets of messages. Each set of messages can provide sequential guidance to the individual to increase a likelihood of the individual adhering and responding to the medical treatment. Each set of messages can have an associated timeline for delivery and messages in the set can be transmitted based on the timeline for delivery.

In an interrelated aspect, data characterizing an individual can be received. Such data can be received at a plurality of sequential stages while the individual is undergoing a treatment regimen. At each stage, variables can be extracted from such data so that it can be determined, using a predictive model populated with the extracted variables, a likelihood of the individual adhering to a treatment regimen. The predictive model can be trained on historical treatment regimen adherence data empirically derived from a plurality of subjects. At each stage, data characterizing the determined likelihood of adherence can be promoted.

In still a further interrelated aspect, data characterizing an individual can be received. Variables from the data can be extracted so that it can be determined, using a predictive model populated with the extracted variables, a likelihood of the individual responding to a treatment regimen. The predictive model can be trained on historical treatment regimen responsiveness data empirically derived from a plurality of subjects. Data characterizing the determined likelihood of responsiveness can be promoted.

Articles are also described that comprise a machine-readable storage medium tangibly embodying instructions that when performed by one or more machines result in operations described herein. Similarly, computer systems are also described that may include a processor and a memory coupled to the processor. The memory may temporarily or permanently store one or more programs that cause the processor to perform one or more of the operations described herein.

The details of one or more variations of the subject matter described herein are set forth in the accompanying drawings and the description below. Other features and advantages of the subject matter described herein will be apparent from the description and drawings, and from the claims.

DETAILED DESCRIPTION

Figure 1:
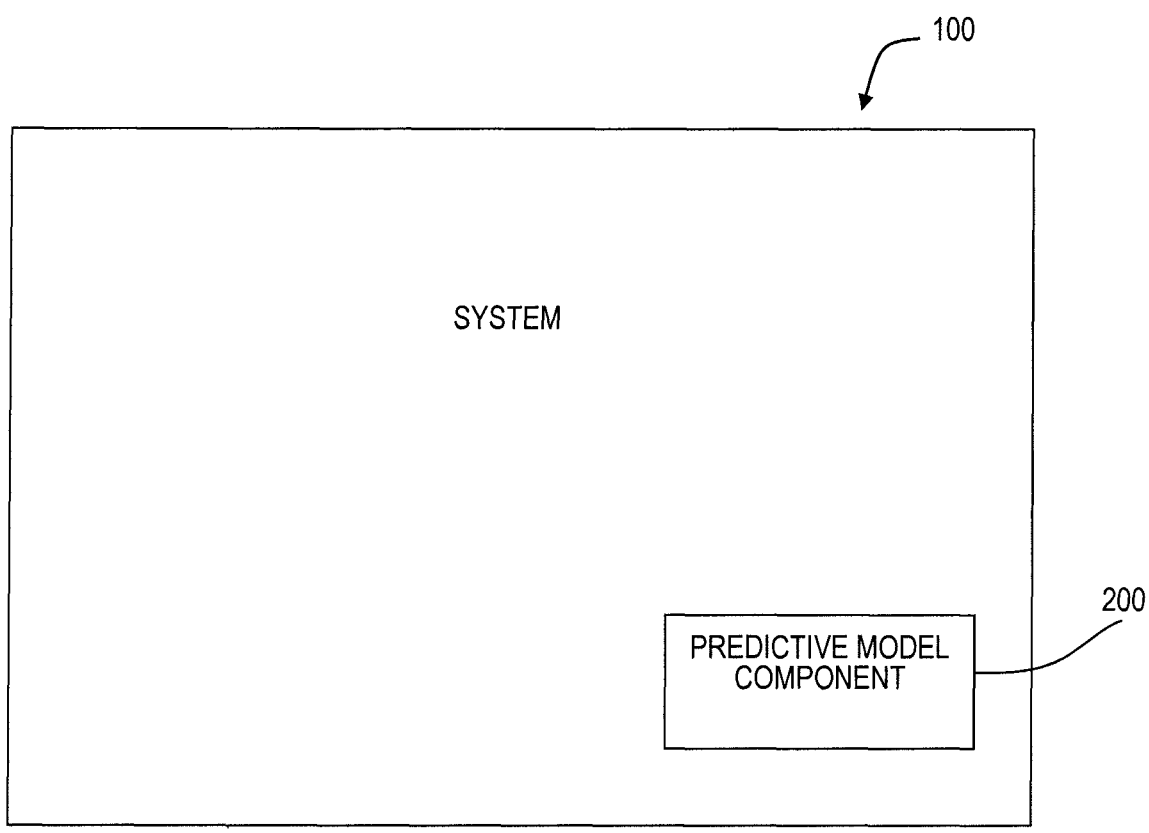
FIG. 1 is a schematic diagram of a computer system.

FIG. 1 is a block diagram of a system 100 that is used to determine or predict a person's potential adherence to a treatment plan, according to an example variation. The system 100 includes at least one predictive model component 200 for producing a model of the person's adherence to a treatment plan over time. The system 100 and the model component 200 can include one or more processors. The predictive model component 200 may include one or more processors. In some instances, the predictive model component 200 may include a portion of a processor.

Figure 2:
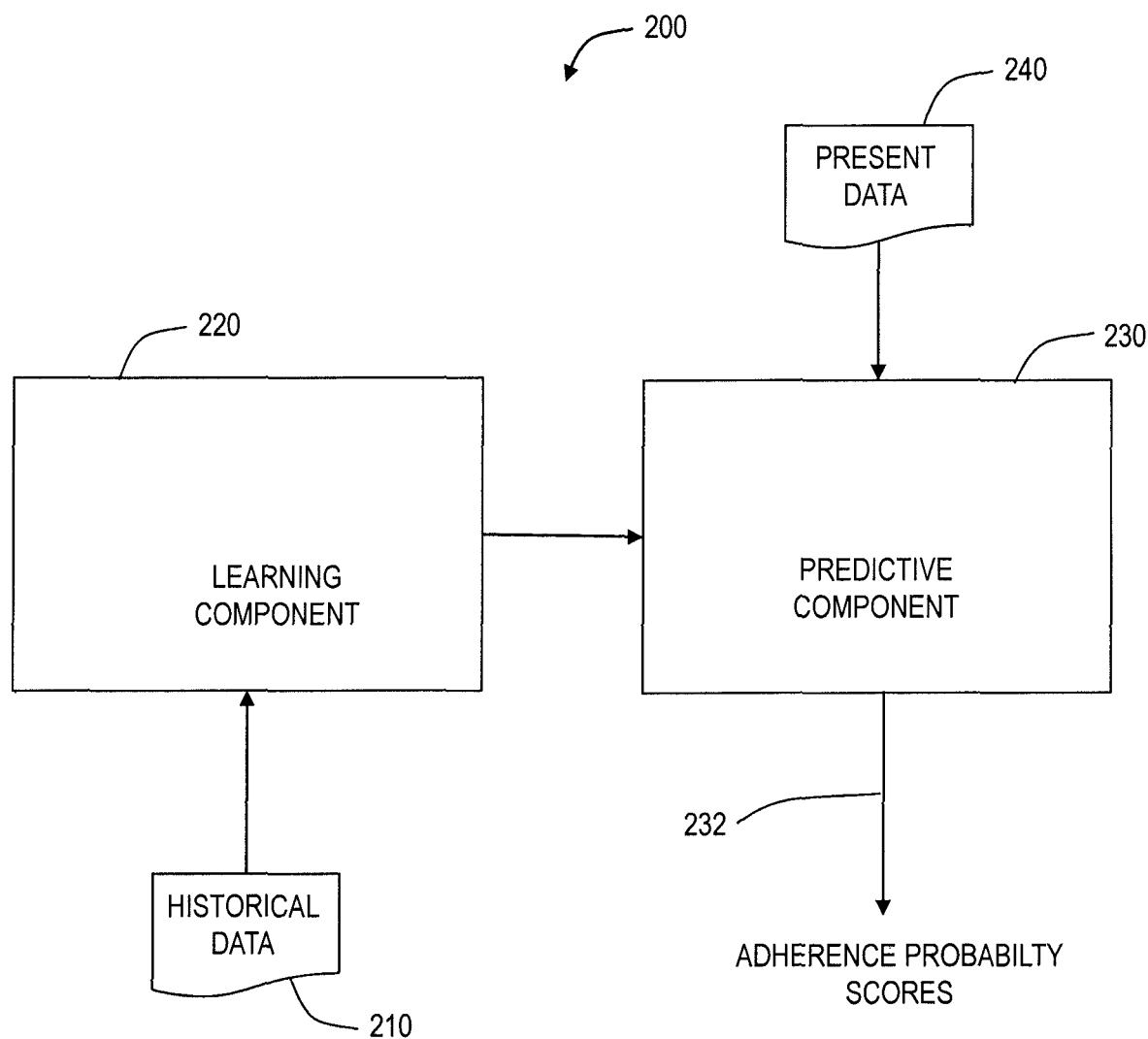
FIG. 2 is a block diagram of an example modeling component.

FIG. 2 is a block diagram of an example modeling component 200 used as may be used in one or more variations of system 100. The modeling component 200 includes a learning component 220 and a predictive component 230. The learning component 220 processes historical data 210. The learning component determines and recognizes various patterns from the historical data 210. In this particular system, the historical data 210 is related to other patients or persons and their adherence to a treatment plan. These treatment plans can be any type of treatment plan. For the sake of an example, the adherence discussed in this document will relate to prescription medications. The historical data 210 related to people and following treatment regimens is searched for patterns. Generally, the search of the historical data yields variables indicative of the probability of adherence to a treatment plan or treatment regimen. In this case, the search of the historical data yields variables indicative of the probability of adherence to following a regimen of prescription medications. Once variables are found, the variables are tested to make sure the historical data can be correlated to the probability of patients and people adhering to their treatment plan, such as following a regimen of prescription medications. In some instances, one variable may be found. In other instances, a plurality of variables may be found. One or more variables may be combined to yield a better correlation than that of a single variable. Generally, the best correlation between the variable and variables and following the treatment plan, such as following a regimen of prescription medications, is found. It should be noted, that the best correlation may include less variables than other models. Generally, a balance between the number of variables selected and the correlation to a treatment plan is determined. It should be noted, that for different treatment plans, different variables may correlate to the treatment plan.

Once the variable or variables are selected, a model is formed. The model can then be used as part of the predictive component 230. The model can be used with present data 240 to predict the likelihood of compliance with a medical treatment regimen or treatment plan. The probability of a particular person can be used to generate an output 232, such as a score, from the predictive component 230. In some implementations, reason codes for the score can also be generated for the particular person or patient as another output 232. The score and the reason codes are possible outputs 232 from the predictive component 230 of the modeling component.

Figure 3:
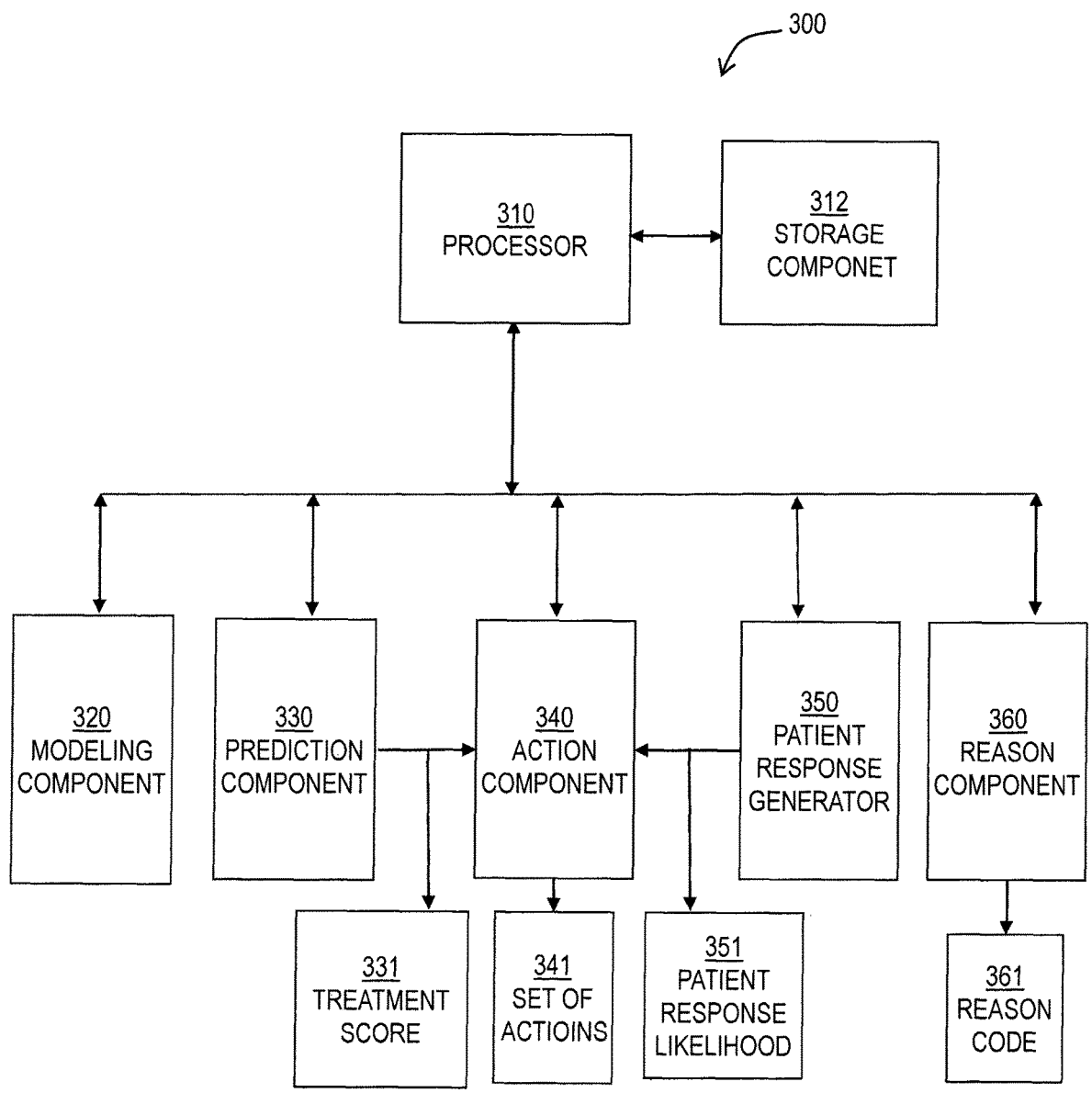
FIG. 3 is a schematic view of another computer system.

FIG. 3 is a schematic view of another computer system 300. The computer system 300 includes a processor 310, a storage component 312 for holding historical data regarding adherence by persons to a medical treatment, and a modeling component 320 that determines at least one variable from the historical data in the storage component. The at least one variable correlates the adherence to medical treatment to the historical data. The computer system also includes a prediction component 330 which determines a likelihood of adherence to a treatment regimen. The modeling component 320 uses the processor 310 and historical data which is stored, at least temporarily, in the storage component 312. The prediction component 330 uses current and past data on the patient, and the processor to make a prediction of future behavior. The prediction component 330 generates a treatment score 331 indicative of the likelihood of adherence to the treatment regimen. The computer system 300 may also include an action component 340 that generates a set of actions that includes at least one of a plurality of messages sent to the person in response to the value of the treatment score 331 generated for the person. The action component 340 generates a set of actions in response to a type of treatment. The type of treatment can be stored in the storage component 312. In still other variations, the computer system 300 further includes a patient response generator 350 for generating likelihood for patient response 351. The output of the likelihood of adherence to a treatment regimen, such as the treatment score 331, and the likelihood for patient response 351 may both be input to the action component 340 to determine a plurality of actions including messages sent to a patient. The computer system 300 can include a reason component 360 for generating at least one reason code 361 accompanying the treatment score. Of course, the reason component 360 may interact with the processor 310, the storage unit 312, the prediction component 330, the action component 340, and the patient response generator 350 to produce reasons for the various outputs from these components. The various components, such as the modeling component 320, the prediction component 330, the action component 340, and the patient response generator 350, may include computer hardware or computer software or both. The various components also may include a part of the processor 310. The processor 310 can be one processor or a plurality of processors. In addition, the various components may include individual processors that may be dedicated to a single component. All the processors, in some variations, work together to form at least a portion of the computer system 300. All of the processors also can access the storage component 312 to obtain the necessary information needed to accomplish particular tasks. The components may also include storage dedicated to the particular component.

The generated scores 331, 341, 351, 361 can then be used to produce follow ups of various types which are designed to keep the patient complying with the course of treatment. The model produced or generated by the modeling component 320 that produces medication adherence scores, can also be combined with other models. For example, as discussed above, the medication adherence score model can be combined with an action based model. This allows certain constrained resources to be optimized based on key objectives. For example, the use of a cell center or the use of an incentive budget for adherence can be maximized by a key objective of the overall health of the patients. The effort can be improved so that the effort invested will generate the most impact.

Figure 4:
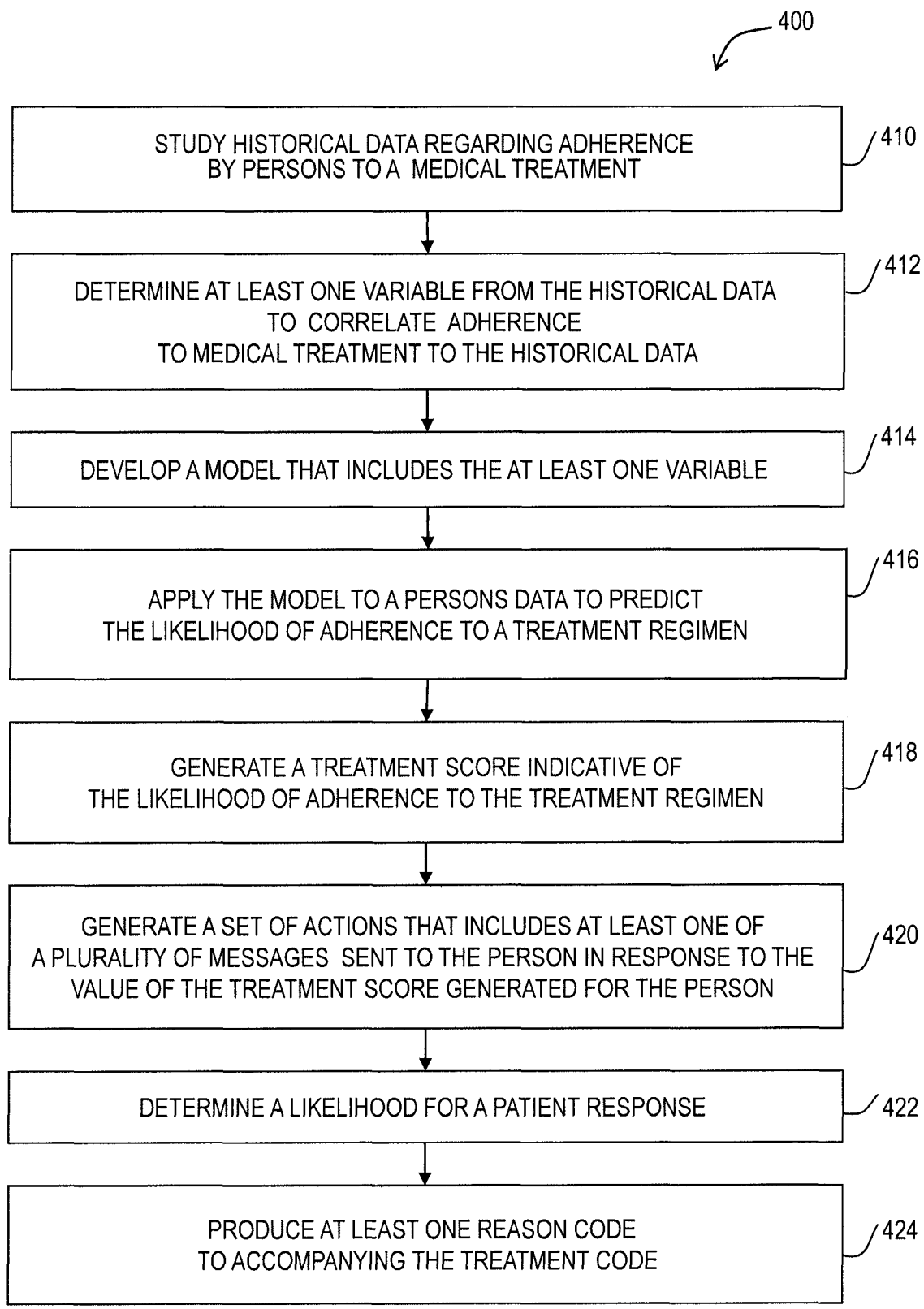
FIG. 4 is a flow diagram of a computerized method for predicting adherence to a medical treatment.

The computer systems 100, 300 can be used to perform a computerized method. FIG. 4 is one example variation of a computerized method 400 for predicting adherence to a medical treatment. The computerized method 400 for predicting adherence to a medical treatment includes studying historical data regarding adherence by persons to a medical treatment 410, determining at least one variable from the historical data that correlates the adherence to medical treatment to the historical data 412, developing a model that includes the at least one variable 414, and applying the model to a persons data predict the likelihood of adherence to a treatment regimen 416. The computerized method further includes generating a treatment score indicative of the likelihood of adherence to the treatment regimen 418. In one variation, the historical data is publicly available data. The computerized method 400 may also include generating a set of actions 420 that includes at least one of a plurality of messages sent to the person in response to the value of the treatment score generated for the person. The set of actions of the computerized method 400 may also a determination of a channel for delivery of the at least one message. In some implementations, the set of actions includes selection of the at least one message from a plurality of messages. In still another variation, the set of actions includes a frequency for delivery of a plurality of messages. In still another variation, the at least one variable varies in response to a type of medical treatment. In still another variation, the computerized method 400 also includes determining likelihood for a patient response 422. The likelihood of adherence to a treatment regimen and the likelihood of the patient response can be used together, in some variations, to determine actions 420, for example. The actions can be messages sent to a patient. In other variations, the computerized method 400 includes producing at least one reason code 424 to accompanying the treatment code.

Figure 5A:
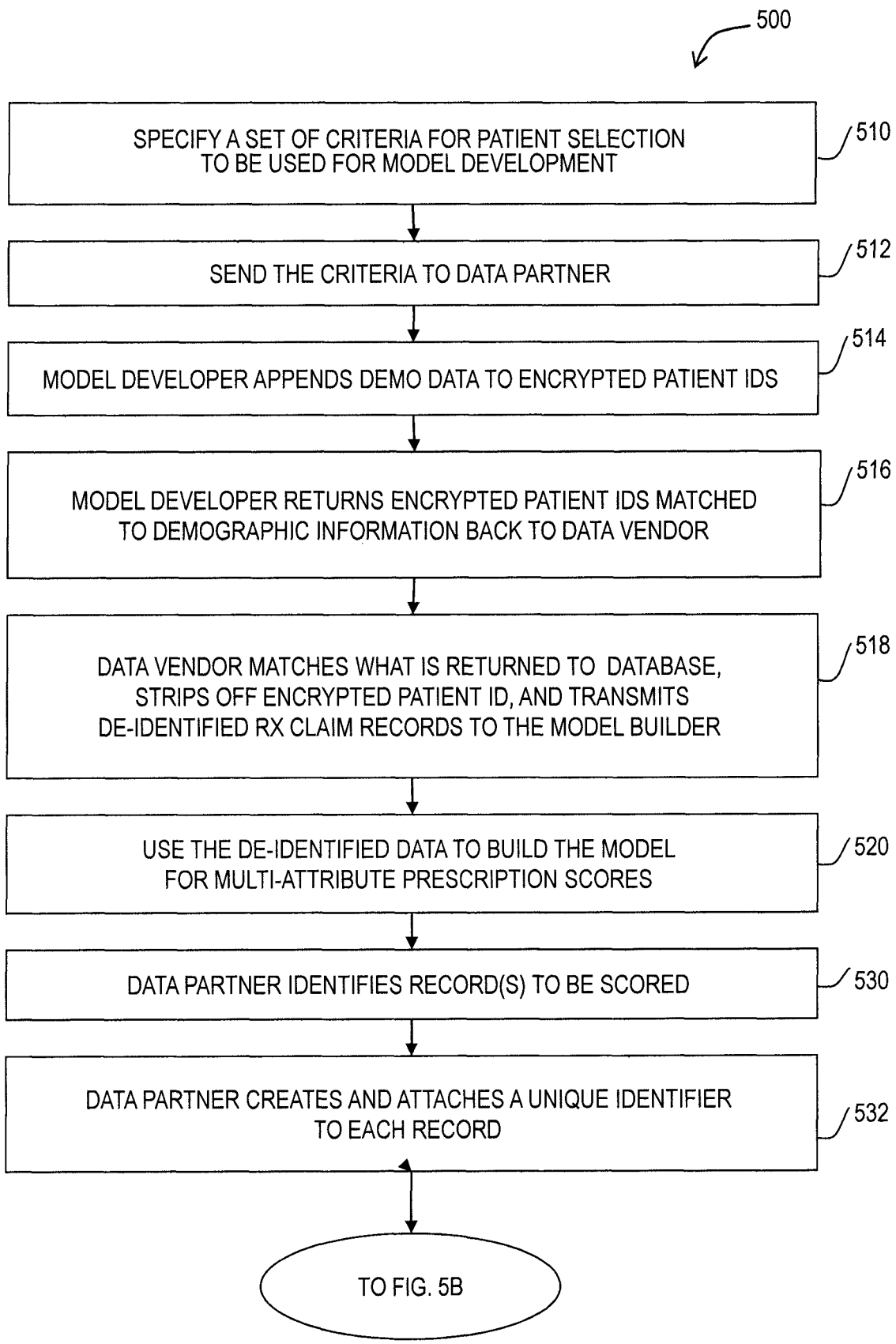
FIGS. 5A and 5B is a flow diagram of another computerized method specifically tailored to pharmaceuticals and is associated with the computer system.
Figure 5B:
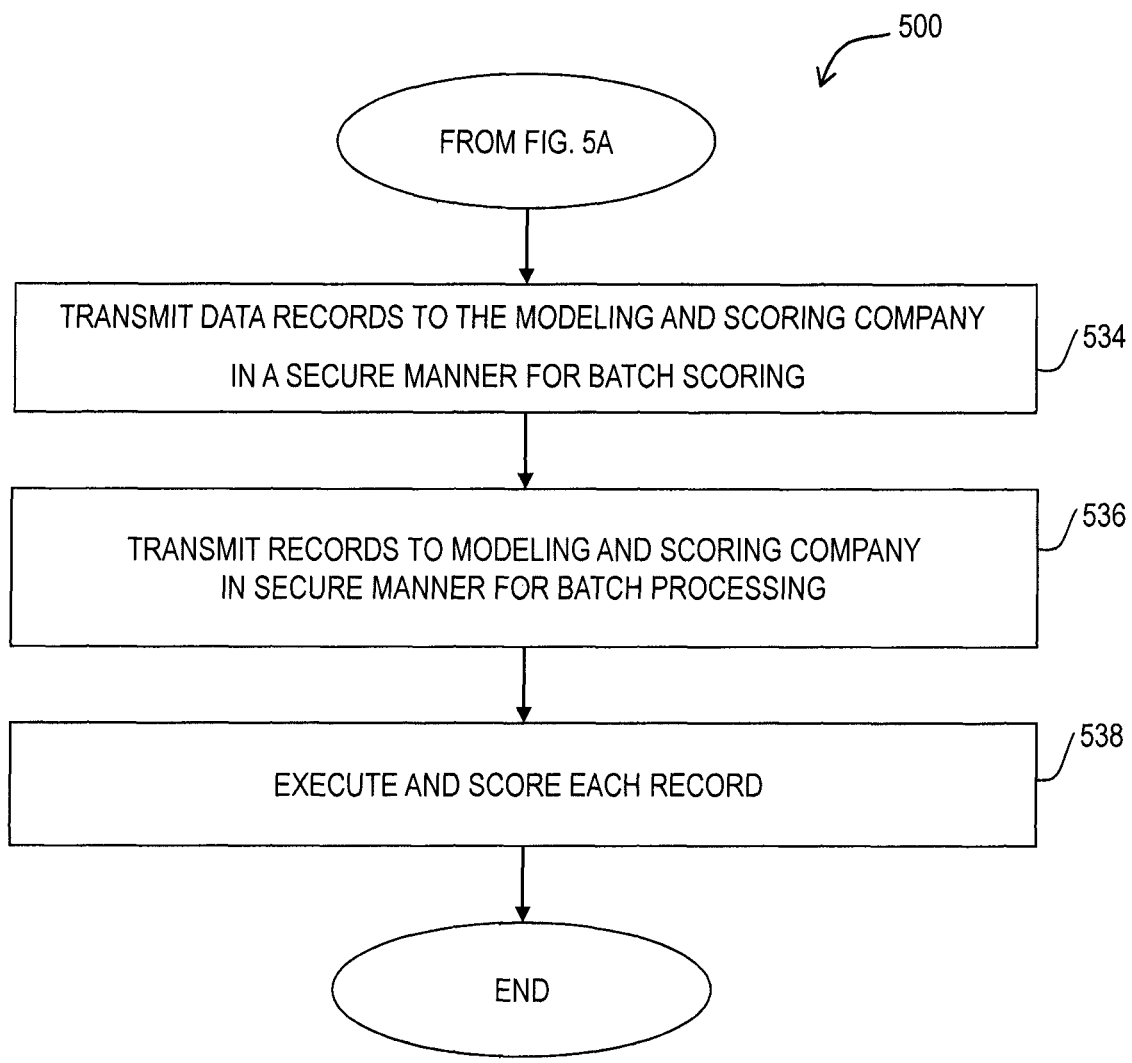

The action based models may also be used to market various treatment plans. In one variation, the actions are used in marketing pharmaceutical products. Developing a model for a pharmaceutical company requires that the prescription data used must not reveal the patient. In such applications, it is necessary to go through additional steps to assure that the patients historical data used to form the model can not be used to determine the identity of the patients. FIG. 5 is an example variation of another method 500 which is specifically tailored to pharmaceuticals. The method 500 includes model development. Model development includes specifying a set of criteria for patient selection to be used for model development 510 and sending the criteria to data partner 512. The data partner selects Rx records and returns only the patient IDs to the model developer. The model developer appends demonstration data to encrypted patient IDs 514 to assure patient anonymity and to prevent re-identification of individuals through this appended demographic information. The model developer returns encrypted patient IDs matched to demographic information back to data vendor 516. Data vendor matches what is returned to them back to their database, strips off encrypted patient ID, and transmits de-identified Rx claim records to the model builder 518. In some variations, the transmission is made in secure mode. The de-identified data to build the model for multi-attribute prescription scores 520.

Scoring and delivering the scores also requires additional steps to keep the data secure. The pharmaceutical company identifies record(s) to be scored 530. The records may come from existing patient base or marketing initiatives. Client creates and attaches a unique identifier to each record 532, and then transmits records to the modeling and scoring company in a secure manner for batch scoring 534. Any required commercially available information can be appended to records 536. The model is then executed to score each record 538. A new record is created that contains only the score and the unique identifier (score record) 540, and this is transmitted (score plus unique identifier) to the pharmaceutical company in a secure manner 542. Of course, the above applications assume that there are a plurality of records. It should be understood that the same process can be applied for use with one record.

Figure 8A:
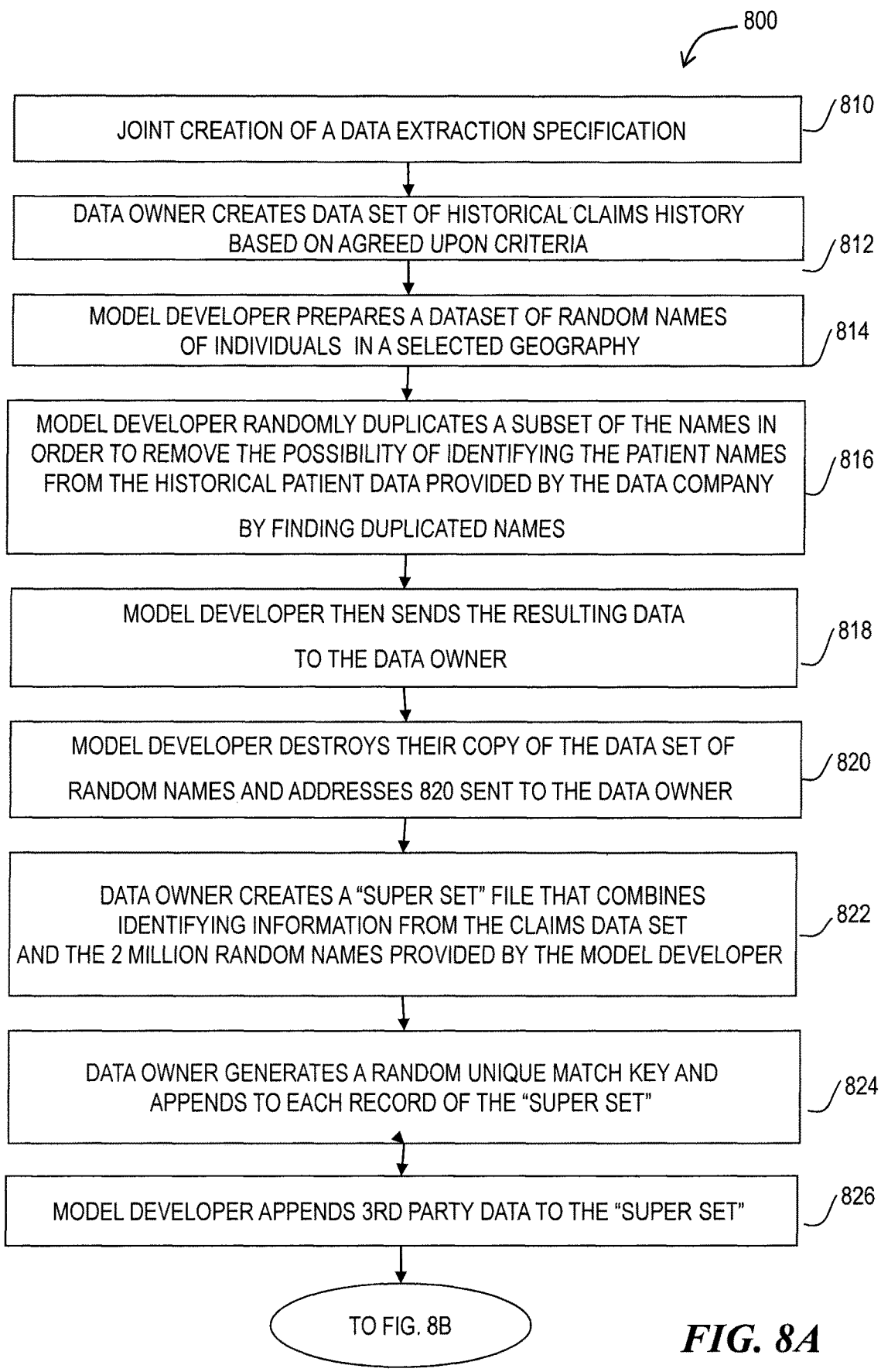
FIGS. 8A and 8B is another example of a computerized method which is specifically tailored to pharmaceuticals.
Figure 8B:
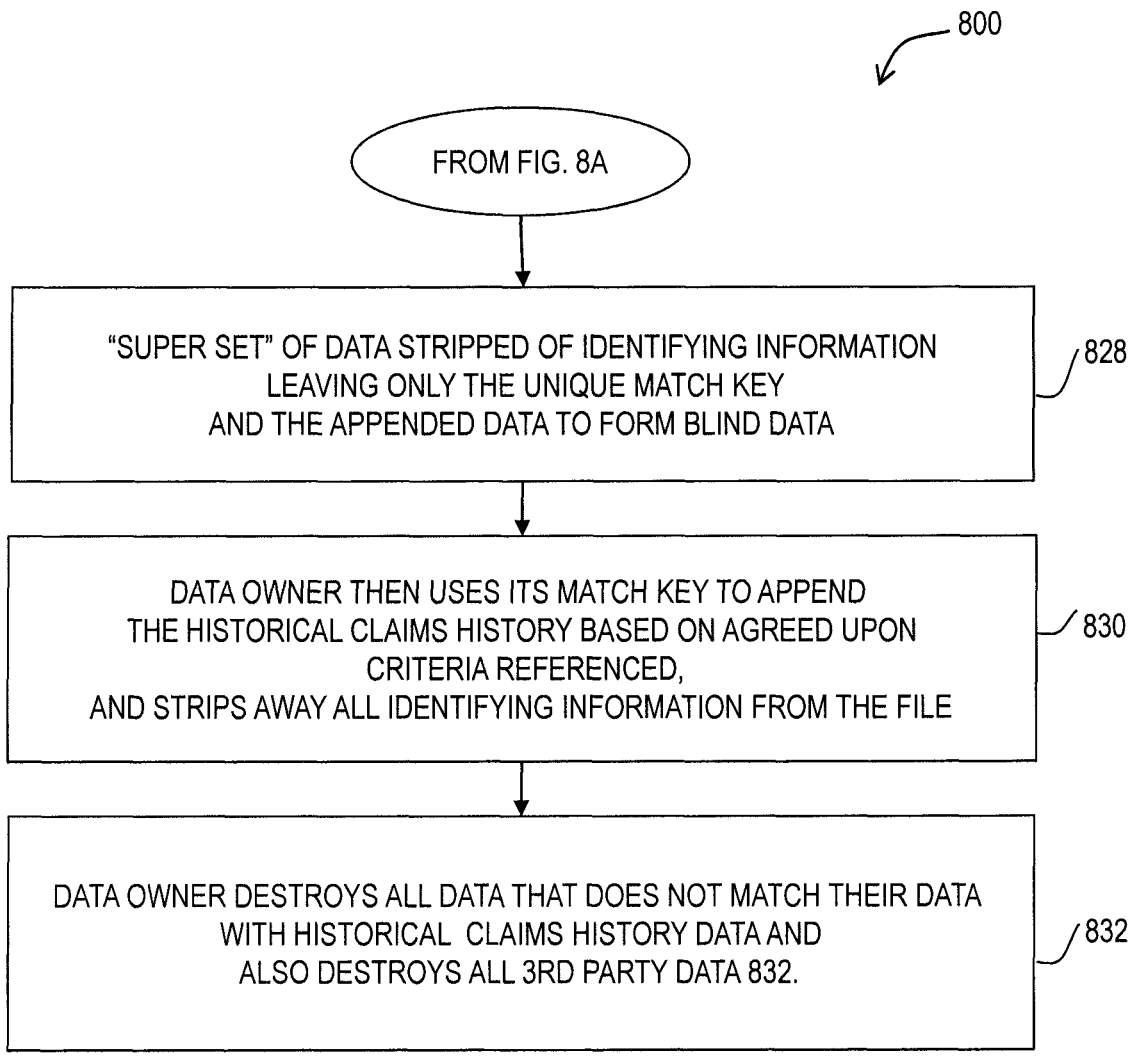

FIGS. 8A and 8B is another example variation of a computerized method 800 for masking the identity of patients from data about them. In the United States this is for meeting a governmental requirement that there is less than a 25% chance of identifying a patient from a data set about patients. The method includes joint creation of a data extraction specification 810. The creation of the data extraction is a joint development between a data owner and a model developer. The data owner creates data set of historical claims history based on agreed upon criteria 812. In one example, historical claims history based on 500,000 individuals. The data owner will remove duplicate patients which may be included in multiple files so that no duplicated names will appear in the patient list created. The model developer prepares a dataset of random names of individuals 814 in a selected geography. The dataset of random names typically will include more than the number of names on the data (historical claims history) the data company provides. In one example, the claims history is related to 500,000 patients and the random name data set includes 2 million individuals. The model developer randomly duplicates a subset of the names in order to remove the possibility of identifying the patient names from the historical patient data provided by the data company by finding duplicated names 816. The model developer then sends the resulting data to the data owner 818. The model developer destroys their copy of the data set of random names and addresses 820 sent to the data owner. The data owner then creates a "super set" file that combines identifying information from the claims data set and the 2 million random names provided by the model developer 822. The data owner then generates a random unique Match Key and appends to each record of the "Super Set" 824. The model developer appends third party data to the "super set" 826. The "super set" is stripped of identifying information leaving only the unique Match Key and the appended data to form blind data 828. Unless authorized by the model developers third party data providers, the model developer will encrypt data fields from all third party data providers except for the Match Key. The data owner then uses its Match Key to append the historical claims history based on agreed upon criteria referenced in step 810, and strips away all identifying information from the file 830. The data owner destroys all data that does not match their data with historical claims history data. The data owner also destroys all third party data 832.

Figure 6:
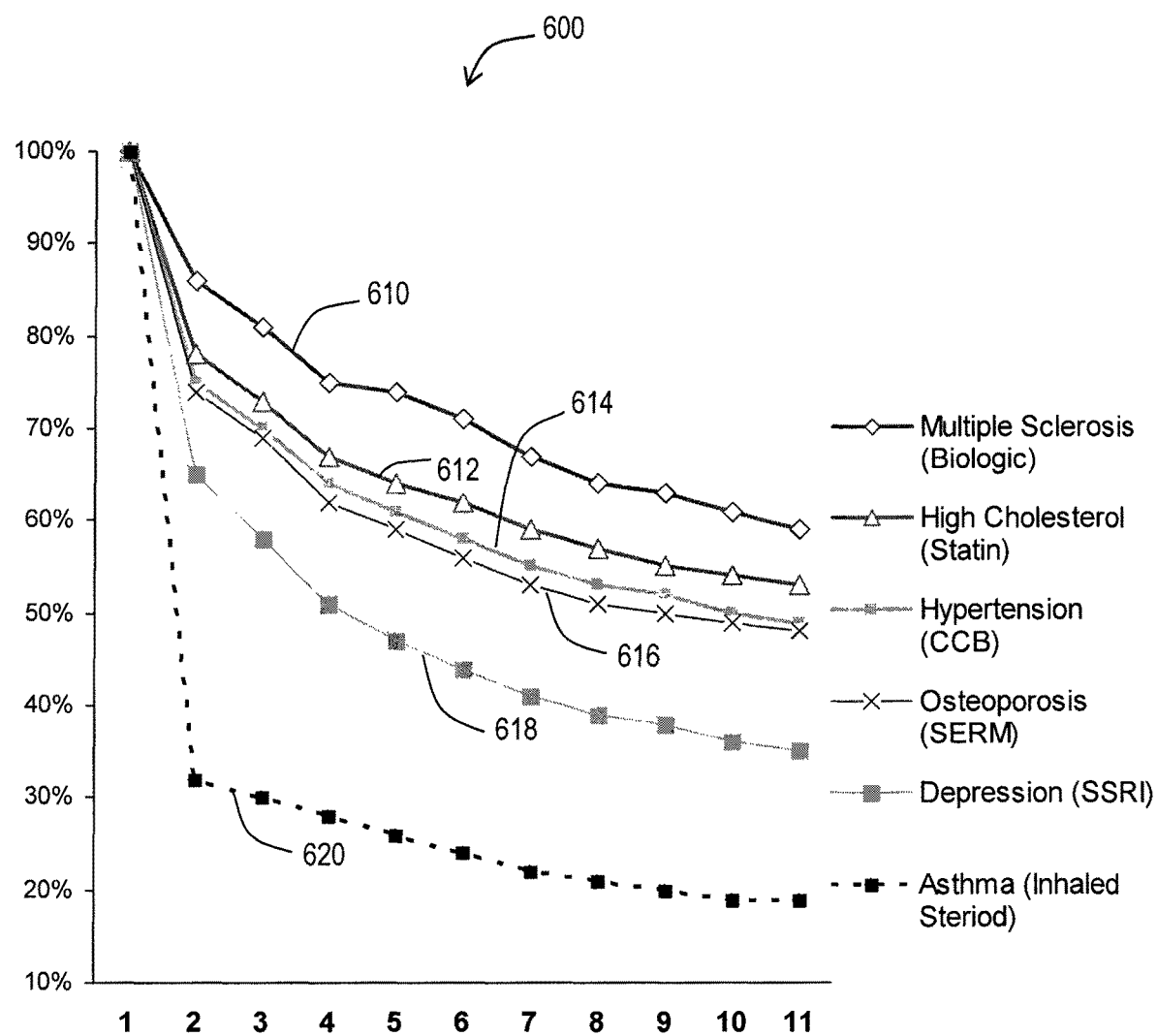
FIG. 6 is a graph of percentage of patients that adhere to various prescription regimens over time, according to an example variation.

Producing a model combats the problem of a drop in adherence to a regimen of prescription medicine. FIG. 6 shows a graph 600 of percentage of those that adhere to various prescription regimens over time. The percentage of patients that adhere to the regimen is shown on the y-axis 610. The time is in units of months, which is shown on the x-axis 620. The graph 600 shows curves 630, 632, 634, 636, 638, 640, 642 for compliance to prescriptions to treat multiple sclerosis, high cholesterol, hypertension, osteoporosis, asthma, respectively. The curves show that most people follow a particular regimen for prescription medication for about two months followed by a significant drop in the percentage of those following the regimen. The number of patients (represented by percentage) who continue to follow the regimen for prescribed drugs then, for the most part, is in a steady state or a state of fairly low decline.

One application of the method and apparatus described above is directed at identifying those individuals that are less likely to follow the regimen of prescribed drugs for a particular ailment. A model is generated. In some variations, extra measures are taken to assure that the historical data used to generate the model can not be used to identify the patients associated with the historical data. Generating the model provides various insights about the patients. Some are known and others are unknown. For example, the model or models capture predictors regarding patient compliance that are consistent with industry knowledge such as age, gender, and geographic location. The model or models also capture additional predictors of adherence that are not well known, such as purchase behavior, income, and credit risk associated with geographic region. Of course, there may be other not well known predictors that may surface in other models. The known and the lesser known predictors can be useful in tailoring messages to particular patients.

Figure 7:
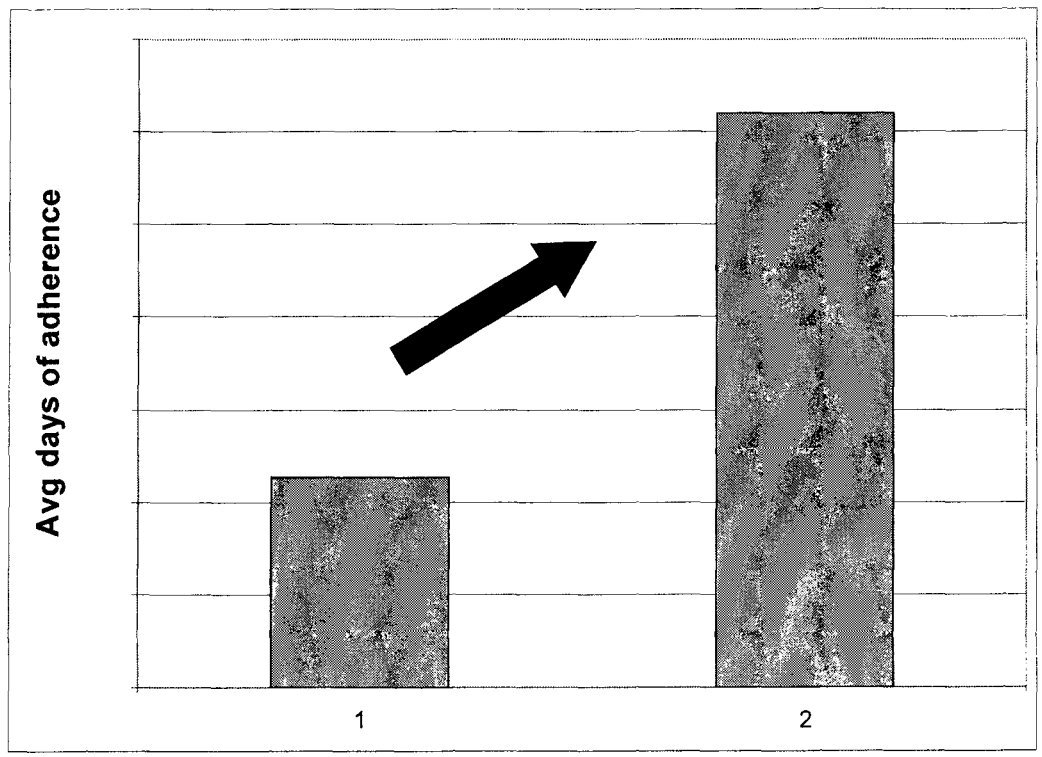
FIG. 7 is a graph showing that the days of adherence to a regimen in first year was increased by 120 days in one case study.

The result of modeling is a score indicative of an observable metric closely related to adherence to a regimen. This allows the pharmaceutical company to have an accurate and objective measure of patient value. Applying the results of modeling and predicting adherence includes sending messages and other information to selected patients that have been prescribed a medication. The pharmaceutical company can then match the right investment (marketing materials, incentives, etc.) to the right patient to achieve improved health for the patient. The pharmaceutical company will also have improved financial outcomes in terms of sales of a particular prescribed drug. The end result, in some instances is that the days of therapy (i.e. adherence to the regimen) was increased substantially in the first year. In one example, shown in FIG. 7, the days of adherence to a regimen in first year was increased by 120 days. The patient's blood pressure was reduced, and product usage increased $240. In other words, the patient was physically healthier and the company selling the product was financially healthier. The insurance company had less cost than if patient did not adhere to the regimen and placed him or herself into an unhealthy state.

A score provides means for managing customers more effectively and consistently across channels, and enables greater precision in segmentation and agility in treatment actions. The score distills complex data into a single metric for operational efficiency, and provides proxy and common lexicon for describing levels of patient adherence across the enterprise. The score also accelerates evaluation of patient value and adherence risk through automation.

It should be noted that the above example pertains to a regimen of prescription medications. This is but one application of the method and apparatus. It should be noted that the method and apparatus are equally applicable to other types of regimens, such as a regimen for therapy. For example, if a patient undergoes knee surgery, there may be a painful yet effective regimen of therapy that needs to be followed in order to rehabilitate the knee. This method and apparatus could be applied to the knee rehabilitation therapy. Another therapy might be physical fitness routines to prevent heart disease or the like. Many fitness centers now include machines that electronically log a person's activity on a weight machine or a cardio machine. This data could be used to indicate adherence to a regimen. When physical activity drops off, messages could be sent to the patient to motivate the person and keep them going.

Figure 9:
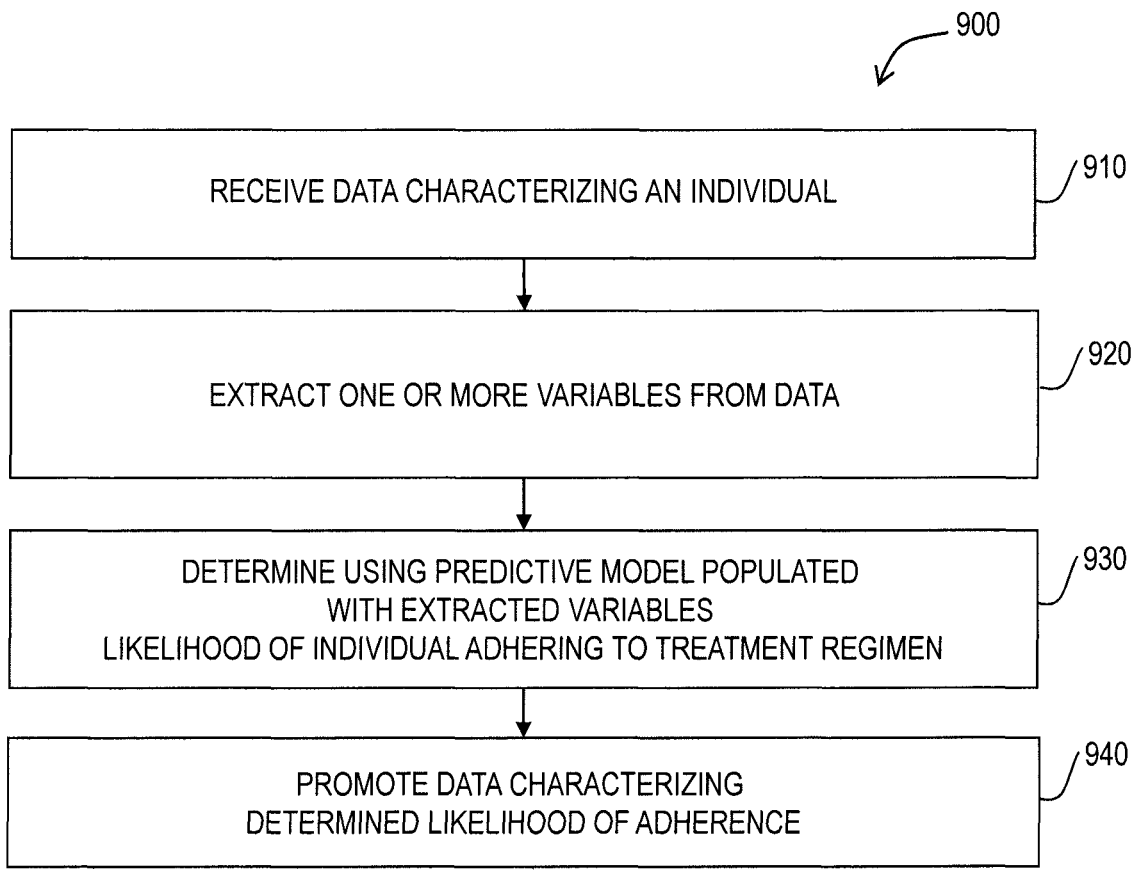
FIG. 9 is a process flow diagram illustrating a method for determining a likelihood of adherence to a medical treatment regimen.

FIG. 9 is a process flow diagram illustrating a method in which, at 910, data characterizing an individual is received. Thereafter, at 920, one or more variables are extracted from the data so that, at 930, using a predictive model populated with the extracted variables, a likelihood of the individual adhering to a treatment regimen can be determined. The predictive model is trained on historical treatment regimen adherence data empirically derived from a plurality of subjects. Subsequently, at 940, data characterizing the determined likelihood of adherence can be promoted.

A variety of predictive models can be utilized with the subject matter described herein. The predictive models used herein to generate the treatment adherence score and/or the patient response score can be based, for example, on a scorecard model developed using the ModelBuilder™ software suite of Fair Isaac Corporation. In some implementations, a divergence-based optimization algorithm can be trained using the medical/adherence data from a plurality of patients. The underlying predictive model can use a variety of predictive technologies, including, for example, neural networks, support vector machines, and the like in order to adherence and/or response of a single individual based on historical data from a large number of subjects.

Various implementations of the subject matter of the method and apparatus described avoe may be realized in digital electronic circuitry, integrated circuitry, specially designed ASICs (application specific integrated circuits), computer hardware, firmware, software, and/or combinations thereof. These various implementations may include implementation in one or more computer programs that are executable and/or interpretable on a programmable system including at least one programmable processor, which may be special or general purpose, coupled to receive data and instructions from, and to transmit data and instructions to, a storage system, at least one input device, and at least one output device.

These computer programs (also known as programs, software, software applications or code) include machine instructions for a programmable processor, and may be implemented in a high-level procedural and/or object-oriented programming language, and/or in assembly/machine language. As used herein, the term "machine-readable medium" refers to any computer program product, apparatus and/or device (e.g., magnetic discs, optical disks, memory, Programmable Logic Devices (PLDs)) used to provide machine instructions and/or data to a programmable processor, including a machine-readable medium that receives machine instructions as a machine-readable signal. The term "machine-readable signal" refers to any signal used to provide machine instructions and/or data to a programmable processor.

To provide for interaction with a user, the method and apparatus described above may be implemented on a computer having a display device (e.g., a CRT (cathode ray tube) or LCD (liquid crystal display) monitor) for displaying information to the user and a keyboard and a pointing device (e.g., a mouse or a trackball) by which the user may provide input to the computer. Other kinds of devices may be used to provide for interaction with a user as well; for example, feedback provided to the user may be any form of sensory feedback (e.g., visual feedback, auditory feedback, or tactile feedback); and input from the user may be received in any form, including acoustic, speech, or tactile input.

The methods and apparatus described and contemplated above may be implemented in a computing system that includes a back-end component (e.g., as a data server), or that includes a middleware component (e.g., an application server), or that includes a front-end component (e.g., a client computer having a graphical user interface or a Web browser through which a user may interact with an implementation of the subject matter of Appendix A), or any combination of such back-end, middleware, or front-end components. The components of the system may be interconnected by any form or medium of digital data communication (e.g., a communication network). Examples of communication networks include a local area network ("LAN"), a wide area network ("WAN"), and the Internet.

The computing system may include clients and servers. A client and server are generally remote from each other and typically interact through a communication network. The relationship of client and server arises by virtue of computer programs running on the respective computers and having a client-server relationship to each other.

Although a few variations have been described and illustrated in detail above, other modifications are possible. For example, the logic flow depicted in the accompanying figures and described herein do not require the particular order shown, or sequential order, to achieve desirable results. Other variations may be within the scope of the following claims.

What is claimed is:

1. A computer-implemented patient treatment method comprising:
   receiving data characterizing a patient under medical treatment to determine treatment adherence patterns for the patient;
   extracting one or more extracted variables from the data, based on the treatment adherence patterns for the patient, the one or more extracted variables comprising a combination of a plurality of variables including one or more of an income of the patient, a credit risk of the patient, and a geographic region of the patient;
   populating a predictive model with the extracted variables;
   training the predictive model on historical treatment regimen adherence data empirically derived from a plurality of patients previously undergoing medical treatment;
   using the predictive model to determine a likelihood of the patient adhering to the treatment regimen;
   using the predictive model to generate a treatment score indicative of the likelihood of adherence to the treatment regimen by the patient, the treatment score lying within a range of treatment scores;
   using the predictive model to generate a patient response score indicative of likelihood of the patient responding to the treatment regimen;
   based on the treatment score and the patient response score, administering to the patient at least a treatment that yields greater precision in segmentation and agility in treatment actions as applied to the particular patient based on the predictive model's evaluation of the particular patient's characteristic against known characteristics of the plurality of patients previously undergoing medical treatment.

2. A method as in claim 1, wherein the computing device associated with the patient displays the at least one message.

3. A method as in claim 1, further comprising:
   determining, using one or more processors, a delivery channel for transmitting the at least one message,
   wherein the at least one message is transmitted to the computing device via the delivery channel.

4. A method as in claim 1, further comprising:
   receiving, using one or more processors, additional data characterizing the patient, at least a portion of the additional data being generated subsequent to initiation by the patient of the treatment regimen;
   extracting, using one or more processors, one or more variables from the additional data, at least one of the variables being affected by initiation of the treatment regimen;
   determining, using one or more processors and using the predictive model populated with the extracted variables from the additional data, a likelihood of the patient continuing to adhere to the treatment regimen; and
   generating, using one or more processors, data characterizing the determined likelihood of the continued adherence.

5. A method as in claim 1, further comprising storing the treatment score.

6. A method as in claim 1, further comprising transmitting the treatment score to a remote server.

7. A method as in claim 1, further comprising:
   determining, using one or more processors, a likelihood for a patient response to the treatment regimen.

8. A method as in claim 7, wherein the determining of the likelihood for a patient response comprises:
   extracting, using one or more processors, one or more patient response variables from the data; and
   determining, using one or more processors and using a second predictive model populated with the extracted patient response variables, a likelihood of the patient responding to the treatment regimen, the second predictive model being trained on historical treatment regimen response data empirically derived from a plurality of subjects, the second predictive model being at least one of a neural network model and a support vector machine model; and
   generating, using one or more processors, data characterizing the determined likelihood of the patient responding to the treatment regimen, the data characterizing determined likelihood of the patient responding to the treatment regimen being different from the data characterizing the determined likelihood of adherence.

9. A method as in claim 8, further comprising:
   generating, using one or more processors, a patient response score indicative of the likelihood of the patient responding to the treatment regimen, the patient response score being separate from the treatment score.

10. A method as in claim 9, further comprising:

associating, using one or more processors, the patient response score with one of a plurality of sets of messages, at least one set of messages providing sequential guidance to the patient to increase a likelihood of the patient responding to the treatment regimen, the at least one set of messages further having an associated timeline for delivery; and transmitting, using one or more processors, messages in the set of messages based on the timeline for delivery.

11. A method as in claim 1, further comprising masking, by one or more processors, the historical treatment regimen adherence data to ensure that the subjects associated with the historical treatment regimen adherence data cannot be identified.

12. A method as in claim 1, wherein the one or more processors form a plurality of models, the one or more processors combining two or more of the plurality of models to optimize constrained computing resources associated with the one or more processors.

\* \* \* \* \*